United States Patent [19]

Yokoyama et al.

[11] Patent Number: 5,346,946

[45] Date of Patent: Sep. 13, 1994

[54] OCULAR LENS MATERIAL

[75] Inventors: Yasuhiro Yokoyama; Noriko Iwata; Eri Ito; Ichiro Ando, all of Nagoya; Shoji Ichinohe; Toshio Yamazaki, both of Annaka, all of Japan

[73] Assignees: Menicon Co., Ltd, Nagoya; Shin-Etsu Chemical Co., Ltd., Tokyo, both of Japan

[21] Appl. No.: 111,452

[22] Filed: Aug. 25, 1993

[30] Foreign Application Priority Data

Aug. 26, 1992 [JP] Japan .................................. 4-227341
Jul. 20, 1993 [JP] Japan .................................. 5-179257

[51] Int. Cl.$^5$ ............................................. C08F 30/08
[52] U.S. Cl. ...................................... 524/547; 526/279
[58] Field of Search ......................... 526/279; 524/547

[56] References Cited

U.S. PATENT DOCUMENTS 4,954,586 9/1990 Nobuyuki et al. .

*Primary Examiner*—Joseph L. Schofer
*Assistant Examiner*—N. Sarofim
*Attorney, Agent, or Firm*—Oblon, Spivak, McClelland, Maier & Neustadt

[57] ABSTRACT

An ocular lens material made of a copolymer comprising, as main copolymerizable components, (A) a polysiloxane macromonomer having polymerizable groups bonded via one or more urethane bonds to the siloxane main chain and (B) an alkyl (meth)acrylamide, wherein the weight ratio of the polysiloxane macromonomer to the alkyl (meth)acrylamide is from 5/95 to 90/10.

7 Claims, No Drawings

OCULAR LENS MATERIAL

The present invention relates to an ocular lens material. More particularly, it relates to an ocular lens material which has high oxygen permeability and high strength and which is useful for e.g. contact lenses, intraocular lenses or artificial cornea.

Heretofore, it has been known that a soft material is usually preferred as a material for contact lenses giving comfortable feeling to wearers, or as a material for intraocular lenses which can be inserted in a modified shape through a small incision of the eye ball without damaging eye tissues.

Such a soft material includes a water-absorptive material which swells and softens upon absorption of water, and a substantially non-water absorptive material. With such a water-absorptive material, the oxygen permeability depends on the water absorptivity, and its oxygen permeability coefficient could never be larger than the oxygen permeability coefficient of water.

In recent years, as a material for obtaining contact lenses which are water-absorptive and excellent in oxygen permeability, a material made of a copolymer of a fluorine-type (meth)acrylate monomer with a hydrophilic monomer such as 2-hydroxyethyl methacrylate, glycerol methacrylate or N,N-dimethylacrylamide, or a material made of a copolymer of such a hydrophilic monomer with a silicon-type (meth)acrylate monomer, has been proposed (Japanese Unexamined Patent Publications No. 179422/1991, No. 196117/1991 and No. 196118/1991).

However, if the amount of the fluorine-type (meth)acrylate monomer or the silicon-type (meth)acrylate monomer is increased in an attempt to further improve the oxygen permeability of the material made of such a copolymer of the fluorine-type (meth)acrylate monomer with the hydrophilic monomer or a copolymer of the silicon-type (meth)acrylate monomer with the hydrophilic monomer, the resulting material will be semi-hard. Accordingly, it will be difficult to obtain contact lenses giving comfortable feeling to wearers or intraocular lenses which can be readily inserted in a deformed shape through a small incision of the eye ball, by using such a material.

In view of the above-mentioned prior art, the present inventors have conducted extensive studies to obtain an ocular lens material which has characteristics such that ① it is excellent in transparency, ② it is excellent also in oxygen permeability, ③ it has practically adequate mechanical strength, ④ it has a relatively good rubber elasticity and is excellent in the dimensional stability, ⑤ it has a practical water-absorptivity (the water content is at least 5%) and is soft in a water-containing state, ⑥ its surface has little tackiness, ⑦ a stain of e.g. lipid scarcely adheres, and ⑧ it can easily be processed by cutting and grinding. As a result, it has been found that a copolymer comprising a certain specific polysiloxane macromonomer and an alkyl (meth)acrylamide as main copolymer components, is provided with such characteristics. The present invention has been accomplished on the basis of this discovery.

Thus, the present invention provides an ocular lens material made of a copolymer comprising, as main copolymerizable components, (A) a polysiloxane macromonomer having polymerizable groups bonded via one or more urethane bonds to the siloxane main chain, of the formula (I):

$$A^1-U^1-S^1-U^2-A^2 \qquad (I)$$

wherein $A^1$ is a group of the formula (II):

$$Y^{21}-R^{31}- \qquad (II)$$

wherein $Y^{21}$ is an acryloyloxy group, a methacryloyloxy group, a vinyl group or an allyl group, and $R^{31}$ is a linear or branched alkylene group having from 2 to 6 carbon atoms;

$A^2$ is a group of the formula (III):

$$-R^{34}-Y^{22} \qquad (III)$$

wherein $Y^{22}$ is an acryloyloxy group, a methacryloyloxy group, a vinyl group or an allyl group, and $R^{34}$ is a linear or branched alkylene group having from 2 to 6 carbon atoms;

$U^1$ is a group of the formula (IV):

$$-X^{21}-E^{21}-X^{25}-R^{32}- \qquad (IV)$$

wherein $X^{21}$ is a covalent bond, an oxygen atom or an alkylene glycol group having from 1 to 6 carbon atoms, $E^{21}$ is —CONH— (provided that in this case, $X^{21}$ is a covalent bond, and $E^{21}$ forms an urethane bond together with $X^{25}$) or a bivalent group derived from a diisocyanate selected from the group consisting of saturated or unsaturated aliphatic, alicyclic and aromatic diisocyanates (provided that in this case, $X^{21}$ is an oxygen atom or an alkylene glycol group having from 1 to 6 carbon atoms, and $E^{21}$ forms an urethane bond together with $X^{21}$ and $X^{25}$), $X^{25}$ is an oxygen atom or an alkylene glycol group having from 1 to 6 carbon atoms, and $R^{32}$ is a linear or branched alkylene group having from 1 to 6 carbon atoms;

$S^1$ is a group of the formula (V):

$$-\left(\underset{R^{24}}{\underset{|}{\overset{R^{23}}{\overset{|}{Si}}}}-O\right)_{\!\!K}\!\!\left(\underset{R^{26}}{\underset{|}{\overset{R^{25}}{\overset{|}{Si}}}}-O\right)_{\!\!L}\!\!\underset{R^{28}}{\underset{|}{\overset{R^{27}}{\overset{|}{Si}}}}- \qquad (V)$$

wherein each of $R^{23}$, $R^{24}$, $R^{25}$, $R^{26}$, $R^{27}$ and $R^{28}$ independently represents an alkyl group having from 1 to 6 carbon atoms, a fluoroalkyl group or a phenyl group, $K$ is an integer of from 1 to 50, and $L$ is an integer of from 0 to $(50-K)$;

$U^2$ is a group of the formula (VI):

$$-R^{33}-X^{26}-E^{22}-X^{22}- \qquad (VI)$$

wherein $R^{33}$ a linear or branched alkylene group having from 1 to 6 carbon atoms, $X^{22}$ is a covalent bond, an oxygen atom or an alkylene glycol group having from 1 to 6 carbon atoms, $X^{26}$ is an oxygen atom or an alkylene glycol group having from 1 to 6 carbon atoms, and $E^{22}$ is —CONH (provided that in this case, $X^{22}$ is a covalent bond, and $E^{22}$ forms an urethane bond together with $X^{26}$) or a bivalent group derived from a diisocyanate selected from the group consisting of saturated or unsaturated aliphatic, alicyclic and aromatic diisocyanates (provided that in this case, $X^{22}$ is an oxygen atom or an alkylene glycol group having from 1 to 6 carbon atoms, and $E^{22}$ forms an urethane bond together with $X^{22}$ and $X^{26}$); and (B) an alkyl (meth)acrylamide, wherein the weight ratio of the polysiloxane macromonomer to the alkyl (meth)acrylamide is from 5/95 to 90/10.

Now, the present invention will be described in detail with reference to the preferred embodiments.

As described above, the ocular lens material of the present invention is made of a copolymer comprising (A) a polysiloxane macromonomer of the formula (I) and (B) an alkyl (meth)acrylamide, as main components, wherein the weight ratio of the polysiloxane macromonomer to the alkyl (meth)acrylamide is from 5/95 to 90/10.

The above polysiloxane macromonomer has elastic bonds called urethane bonds and is a component which imparts a nature to improve the mechanical strength by reinforcing the material by the siloxane moieties of this monomer without impairing the flexibility and oxygen permeability of the material and by imparting elastic resiliency to eliminate brittleness. Further, the above polysiloxane macromonomer imparts high oxygen permeability, since it has silicone chains in its molecular chain.

The above polysiloxane macromonomer has polymerizable groups at both terminals of the molecule and is capable of being copolymerized with other copolymerizable component by such polymerizable groups. Thus, it has an excellent characteristic such that it imparts a reinforcing effect by chemical bonds (covalent bonds) in addition to the physical reinforcing effect by entanglement of molecules, to the resulting ocular lens.

The above polysiloxane macromonomer is a compound of the formula (I).

As mentioned above, in the formula (I), $A^1$ is a group of the formula (II):

$$Y^{21}-R^{31}-\quad\quad(II)$$

wherein $y^{21}$ and $R^{31}$ are as defined above, and $A^2$ is a group of the formula (III):

$$-R^{34}-Y^{22}\quad\quad(III)$$

wherein $y^{22}$ and $R^{34}$ are as defined above.

Each of $y^{21}$ and $y^{22}$ is a polymerizable group and is preferably an acryloyloxy group, a methacryloyloxy group or a vinyl group in that it is readily copolymerizable with an alkyl (meth)acrylamide.

Each of $R^{31}$ and $R^{34}$ is a $C_{2-6}$ linear or branched alkylene group, preferably an ethylene group, a propylene group or a butylene group.

Each of $U^1$ and $U^2$ is a group containing a urethane bond in the molecular chain of the above polysiloxane macromonomer.

In $U^1$ and $U^2$, each of $E^{21}$ and $E^{22}$ is as mentioned above, —CONH— or a bivalent group derived from a diisocyanate selected from the group consisting of saturated or unsaturated aliphatic, alicyclic and aromatic diisocyanates. Here, the bivalent group derived from a diisocyanate selected from the group consisting of saturated or unsaturated aliphatic, alicyclic and aromatic diisocyanates may, for example, be a bivalent group derived from a saturated aliphatic diisocyanate such as ethylene diisocyanate, 1,3-diisocyanatepropane or hexamethylene diisocyanate; a bivalent group derived from an alicyclic diisocyanate such as 1,2-diisocyanate cyclohexane, bis(4-isocyanatecyclohexyl)methane or isophorone diisocyanate; a bivalent group derived from an aromatic diisocyanate such as tolylene diisocyanate or 1,5-diisocyanate naphthalene; or a bivalent group derived from an unsaturated aliphatic diisocyanate such as 2,2′-diisocyanate diethylfumarate. Among them, a bivalent group derived from hexamethylene diisocyanate, a bivalent group derived from tolylene diisocyanate and a bivalent group derived from isophorone diisocyanate are preferred, since they are relatively readily available, and they are capable of imparting mechanical strength.

In $U^1$, when $E^{21}$ is a —NHCO— group, $X^{21}$ is a covalent bond, and $E^{21}$ forms an urethane bond of the formula —OCO—NH— together with $X^{25}$. Further, when $E^{21}$ is the above-mentioned bivalent group derived from a diisocyanate, $X^{21}$ is an oxygen atom or a $C_{1-6}$ alkylene glycol group, and $E^{21}$ forms an urethane bond together with $X^{21}$ and $X^{25}$. $X^{25}$ is an oxygen atom or a $C_{1-6}$ alkylene glycol group, and $R^{32}$ is a $C_{1-6}$ linear or branched alkylene group.

In $U^2$, $R^{33}$ is a $C_{1-6}$ linear or branched alkylene group. $X^{26}$ is an oxygen atom or a $C_{1-6}$ alkylene glycol group. When $E^{22}$ is a —CONH— group, $X^{22}$ is a covalent bond, and $E^{22}$ forms a urethane bond of the formula —OCO—NH— together with $X^{26}$. Further, when $E^{22}$ is the above-mentioned bivalent group derived from a diisocyanate, $X^{22}$ is an oxygen atom or a $C_{1-6}$ alkylene glycol group, and $E^{22}$ forms a urethane bond together with $X^{22}$ and $X^{26}$.

Here, the $C_{1-6}$ alkylene glycol for the above $X^{21}$, $X^{25}$, $X^{22}$ and $X^{26}$ may, for example, be a group of the formula (VII):

$$-O-(C_xH_{2x}-O)_y-\quad\quad(VII)$$

wherein x is an integer of from 1 to 4, and y is an integer of from 1 to 5. In such a formula (VII), if y is an integer of 6 or more, the oxygen permeability tends to be low, and the mechanical strength tends to deteriorate. Therefore, in the present invention, it is preferred that y is an integer of from 1 to 5, particularly preferably an integer of from 1 to 3.

As mentioned above, $S^1$ is a group of the formula (V). In the formula (V), each of $R^{23}$, $R^{24}$, $R^{25}$, $R^{26}$, $R^{27}$ and $R^{28}$ independently represents a $C_{1-6}$ alkyl group, a fluoroalkyl group or a phenyl group, as mentioned above.

Specific examples of the fluoroalkyl group include, for example, a 3,3,3-trifluoro-n-propyl group, a 3,3,3-trifluoroisopropyl group, a 3,3,3-trifluoro-n-butyl group, a 3,3,3-trifluoroisobutyl group, a 3,3,3-trifluoro-sec-butyl group, a 3,3,3-trifluoro-tert-butyl group, a 3,3,3-trifluoro-n-pentyl group, a 3,3,3-trifluoroisopentyl group, a 3,3,3-trifluorothiopentyl group, and a 3,3,3-trifluorohexyl group. In the present invention, when a polysiloxane macromonomer having such a fluoroalkyl group is employed, and the amount of such a polysiloxane macromonomer is increased, the lipid stain resistance of the resulting ocular lens material tends to be improved.

K is an integer of from 1 to 50, and L is an integer of from 0 to (50 − K). When K +L is larger than 50, the molecular weight of the polysiloxane macromonomer tends to be too large, and the compatibility thereof with an alkyl (meth)acrylamide tends to be poor, whereby there will be a tendency that it does not adequately dissolve when mixed, and white turbidity will result during the polymerization, and it tends to be difficult to obtain a uniform transparent ocular lens material. Further, when it is 0, not only the oxygen permeability of the resulting ocular lens material tends to be low, but also the flexibility tends to be poor. K + L is preferably an integer of from 2 to 40, more preferably from 3 to 30.

The above-mentioned alkyl (meth)acrylamide is a component which imparts transparency and lipid stain resistance to the resulting ocular lens material, improves the water absorptivity of the material and facilitates the cutting and grinding operations.

Such an alkyl (meth)acrylamide may, for example, be N,N-dimethyl (meth)acrylamide, N,N-dimethylaminopropyl methacrylamide or N-isopropyl (meth)acrylamide. These may be used alone or in combination as a mixture of two or more of them. Among them, N,N-dimethylacrylamide is preferred in that it is thereby possible to obtain a water absorptive ocular lens material which is superior in the transparency and which can readily be processed by cutting or grinding.

In this specification, the term "(meth)acrylamide" means "acrylamide and/or methacrylamide".

The weight ratio of the above polysiloxane macromonomer to the alkyl (meth)acrylamide (i.e. polysiloxane macromonomer/alkyl (meth)acrylamide) is usually from 5/95 to 90/10, preferably from 10/90 to 90/10, more preferably from 10/90 to 80/20, most preferably from 15/85 to 60/40. If the proportion of the polysiloxane macromonomer is smaller than the above range, the oxygen permeability of the resulting ocular lens material tends to be inadequate, the mechanical strength or rubber elasticity tends to be low, and the dimensional stability tends to be poor. On the other hand, if the proportion of the polysiloxane macromonomer exceeds the above range, the proportion of the alkyl (meth)acrylamide decreases relatively, whereby the resulting ocular lens material tends to be turbid, the surface tends to be tacky, the lipid-stain resistance tends to be low, the water absorptivity tends to be poor, and the cutting or grinding operation tends to be difficult.

Further, it is desired that the total amount of the polysiloxane macromonomer and the alkyl (meth)acrylamide is at least 25% by weight, preferably at least 30% by weight, more preferably at least 35% by weight, based on the total amount of copolymerizable components. If such a total amount is less than 25% by weight, the resulting ocular lens material tends to be hardly processed by cutting, whereby the or grinding and tends to be tacky.

In the present invention, a silicon-containing monomer selected from the group consisting of a silicon-containing alkyl (meth)acrylate and a silicon-containing styrene derivative may be used as a further copolymerizable component for the purpose of supplementally increasing the oxygen permeability and improving the mechanical strength.

Such a silicon-containing alkyl (meth)acrylate may, for example, be trimethylsiloxydimethylsilylmethyl (meth)acrylate, trimethylsiloxydimethylsilylpropyl (meth)acrylate, methylbis(trimethylsiloxy)silylpropyl (meth)acrylate, tris(trimethylsiloxy)silylpropyl (meth)acrylate, mono[methylbis(trimethylsiloxy)siloxy]bis trimethylsiloxy)silylpropyl (meth)acrylate, tris[methylbis(trimethylsiloxy)siloxy]silylpropyl (meth)acrylate, methylbis(trimethylsiloxy)silylpropylglyceryl (meth)acrylate, tris(trimethylsiloxy)silylpropylglyceryl (meth)acrylate, mono[methylbis(trimethysiloxy)siloxy]bis(-trimethylsiloxy) silylpropylglyceryl (meth)acrylate, trimethylsilylethyltetramethyldisiloxypropylglyceryl (meth)acrylate, trimethylsilylmethyl (meth)acrylate, trimethylsilylpropyl (meth)acrylate, trimethylsilylpropylglyceryl (meth)acrylate, trimethysiloxydimethylsilylpropylglyceryl (meth)acrylate, methylbis(-trimethylsiloxy)silylethyltetramethyldisiloxymethyl (meth)acrylate, tetramethyltriisopropylcyclotetrasiloxanylpropyl (meth)acrylate or tetramethyltriisopropylcyclotetrasiloxybis(trimethylsiloxy)silylpropyl (meth)acrylate.

In this specification, "(meth)acrylate" means "acrylate and/or methacrylate", and the same applies to other (meth)acrylate derivatives.

The above-mentioned silicon-containing styrene derivative may, for example, be a compound of the formula (VIII):

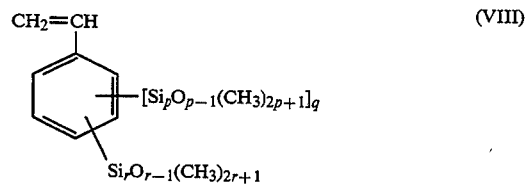

wherein p is an integer of from 1 to 15, q is 0 or 1, and r is an integer of from 1 to 15. With respect to the silicon-containing styrene derivative of the formula (VIII), if p or r is an integer of 16 or more, synthesis and purification of such a derivative tend to be difficult, and the hardness of the resulting ocular lens material tends to be low, and if q is an integer of 2 or more, preparation of such an organopolysiloxane-containing styrene derivative tends to be difficult.

Typical examples of the compound of the formula (VIII) include tris(trimethylsiloxy)silylstyrene, bis(-trimethylsiloxy)methylsilylstyrene, (trimethylsiloxy)-dimethylsilylstyrene, tris(trimethylsiloxy)siloxydimethylsilylstyrene, [bis(trimethylsiloxy)methylsiloxy]-dimethylsilylstyrene, (trimethylsiloxy)dimethylsilylstyrene, heptamethyltrisiloxanylstyrene, nonamethyltetrasiloxanylstyrene, pentadecamethylheptasiloxanylstyrene, heneicosamethyldecasiloxanylstyrene, heptacosamethyltridecasiloxanylstyrene, hentriacontamethylpentadecasiloxanylstyrene, trimethylsiloxypentamethyldisiloxymethylsilylstyrene, tris(pentamethyldisiloxy)silylstyrene, tris(trimethylsiloxy)siloxybis(-trimethylsiloxy)silylstyrene, bis(heptamethyltrisiloxy)-methylsilylstyrene, tris[methylbis(trimethylsiloxy)siloxy]silylstyrene, trimethylsiloxybis[tis(trimethylsiloxy)-siloxy]silylstyrene, heptakis(trimethylsiloxy)trisiloxanylstyrene, nonamethyltetrasiloxyundecylmethylpentasiloxymethylsilylstyrene, tris[tris(trimethylsiloxy)-siloxy]silylstyrene, (tristrimethylsiloxyhexamethyl)tetrasiloxy[tris(trimethylsiloxy)siloxy]trimethylsiloxysilylstyrene, nonakis(trimethylsiloxy)tetrasiloxanylstyrene, bis(tridecamethylhexasiloxy)methylsilylstyrene, heptamethylcyclotetrasiloxanylstyrene, heptamethylcyclotetrasiloxybis(trimethylsiloxy)silylstyrene, tripropyltetramethylcyclotetrasiloxanylstyrene and trimethylsilylstyrene.

These silicon-containing monomers may be used alone or in combination as a mixture of two or more of them. Among such silicon-containing monomers, a silicon-containing alkyl (meth)acrylate such as tris(trimethylsiloxy)silylpropyl (meth)acrylate is preferably employed in that it is thereby at least possible to obtain an ocular lens material having good mechanical strength without decreasing the oxygen permeability. Further, a silicon-containing styrene derivative such as tris(trimethylsiloxy)silylstyrene is preferably employed in that it is thereby possible to obtain an ocular lens material having excellent transparency and good mechanical strength within a wide range of its proportion and having a relatively high refractive index, and by virtue of the high refractive index, it is possible to prepare a thin ocular lens with the same power, whereby it is possible to obtain a contact lens having excellent oxygen permeability corresponding to the thickness being thin.

It is advisable that the amount of such a silicon-containing monomer is not more than 75% by weight, preferably not more than 70% by weight, more preferably not more than 65% by weight, based on the total amount of copolymerizable components. If the amount of such a silicon-containing monomer exceeds 75% by weight, the total amount of the polysiloxane macromonomer and the alkyl (meth)acrylamide will be relatively small, whereby it tends to be difficult to obtain the desired ocular lens material of the present invention. On the other hand, such a silicon-containing monomer is preferably used at least 10% in order to adequately obtain the effect of the incorporation of such silicon-containing monomer.

In the present invention, the copolymer is obtained by using the polysiloxane macromonomer and the alkyl (meth)acrylamide as main components and the siloxane monomer as a further copolymerizable component, as the case requires. However, a monomer having an unsaturated double bond copolymerizable with such copolymerizable components may be used as an additional copolymer component.

Such an additional copolymer component may be used for the purpose of imparting hardness or softness and lipid stain resistance, to the resulting ocular lens material, adjusting the water absorptivity of the material, imparting improved strength and durability by crosslinking, imparting an ultraviolet ray absorbing ability, or imparting a color.

For example, in order to impart hardness, or softness or flexibility by adjusting the degree of hardness, one or more members may be selected for use among linear, branched or cyclic alkyl (meth)acrylates, alkoxyalkyl (meth)acrylates and alkylthioalkyl (meth)acrylates, such as methyl (meth)acrylate, ethyl (meth)acrylate, isopropyl (meth)acrylate, n-propyl (meth)acrylate, isobutyl (meth)acrylate, n-butyl (meth)acrylate, 2-ethylhexyl (meth)acrylate, n-octyl (meth)acrylate, n-decyl (meth)acrylate, n-dodecyl (meth)acrylate, t-butyl (meth)acrylate, pentyl (meth)acrylate, t-pentyl (meth)acrylate, hexyl (meth)acrylate, heptyl (meth)acrylate, nonyl (meth)acrylate, stearyl (meth)acrylate, cyclopentyl (meth)acrylate, cyclohexyl (meth)acrylate, 2-ethoxyethyl (meth)acrylate, 3-ethoxypropyl (meth)acrylate, 2-methoxyethyl (meth)acrylate, 3-methoxypropyl (meth)acrylate, ethylthioethyl (meth)acrylate and methylthioethyl (meth)acrylate; styrene; α-methylstyrene; alkylstyrenes such as methylstyrene, ethylstyrene, propylstyrene, butylstyrene, t-butylstyrene, isobutylstyrene and pentylstyrene; and alkyl-α-methylstyrenes such as methyl-α-methylstyrene, ethyl-α-methylstyrene, propyl-α-methylstyrene, butyl-α-methylstyrene, t-butyl-α-methylstyrene, isobutyl-α-methylstyrene and pentyl-α-methylstyrene. The amount of such an additional copolymer component is usually not more than 60% by weight, preferably not more than 50% by weight, more preferably not more than 40% by weight, based on the total amount of copolymerizable components. If such an amount exceeds 60% by weight, the amount of the above polysiloxane macromonomer tends to be relatively small, whereby the oxygen permeability and the mechanical strength tend to be low.

Further, in order to adjust the water absorptivity of the resulting ocular lens material, hydroxyalkyl (meth)acrylates such as 2-hydroxyethyl (meth)acrylate, hydroxybutyl (meth)acrylate and hydroxypropyl (meth)acrylate; (alkyl)aminoalkyl (meth)acrylates such as 2-dimethylaminoethyl (meth)acrylate and 2-butylaminoethyl (meth)acrylate; polyglycol mono(meth)acrylates such as propyleneglycol mono(meth)acrylate; vinylpyrrolidone; (meth)acrylic acid; maleic anhydride; fumaric acid; fumaric acid derivatives; aminostyrene and hydroxystyrene, may be used alone or in combination as a mixture of two or more. The amount of such an additional copolymerizable component is usually not more than 50% by weight, preferably not more than 30% by weight, more preferably not more than 20% by weight, based on the total amount of copolymerizable components. If such an amount exceeds 50% by weight, the amount of the polysiloxane macromonomer tends to be relatively small, whereby high oxygen permeability and high mechanical strength tend to be hardly be expected.

Further, in order to impart lipid stain resistance to the resulting ocular lens material, a fluorine-containing monomer of the formula (IX):

$$CH_2=CR^4COOC_sH_{(2s-t+1)}F_t \qquad (IX)$$

wherein $R^4$ is a hydrogen atom or $CH_3$, s is an integer of from 1 to 15, and t is an integer of from 1 to $(2s+1)$, may, for example, be employed.

Specific examples of the monomer of the above formula (IX) include 2,2,2-trifluoroethyl (meth)acrylate, 2,2,3,3-tetrafluoropropyl (meth)acrylate, 2,2,3,3-tetrafluoro-t-pentyl (meth)acrylate, 2,2,3,4,4,4-hexafluorobutyl (meth)acrylate, 2,2,3,4,4,4-hexafluoro-t-hexyl (meth)acrylate, 2,3,4,5,5,5-hexafluoro-2,4-bis(trifluoromethyl)pentyl (meth)acrylate, 2,2,3,3,4,4-hexafluorobutyl (meth)acrylate, 2,2,2,2',2',2'-hexafluoroisopropyl (meth)acrylate, 2,2,3,3,4,4,4-heptafluorobutyl (meth)acrylate, 2,2,3,3,4,4,5,5-octafluoorpentyl (meth)acrylate, 2,2,3,3,4,4,5,5,5-nonafluoropentyl (meth)acrylate, 2,2,3,3,4,4,5,5,6,6,7,7-dodecafluoroheptyl (meth)acrylate, 3,3,4,4,5,5,6,6,7,7,8,8-dodecafluorooctyl (meth)acrylate, 3,3,4,4,5,5,6,6,7,7,8,8,8-tridecafluorooctyl (meth)acrylate, 2,2,3,3,4,4,5,5,6,6,7,7,7-tridecafluoroheptyl 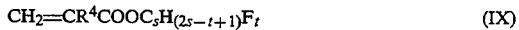 (meth)acrylate, 3,3,4,4,5,5,6,6,7,7,8,8,9,9,10,10-hexadecafluorodecyl (meth)acrylate, 3,3,4,4,5,5,6,6,7,7,8,8,9,9,10,10,10-heptadecafluorodecyl (meth)acrylate, 3,3,4,4,5,5,6,6,7,7,8,8,9,9,10,10,11,11-octadecafluoroundecyl (meth)acrylate, 3,3,4,4,5,5,6,6,7,7,8,8,9,9,10,10,11,11,11-nonadecafluoroundecyl (meth)acrylate, and 3,3,4,4,5,5,6,6,7,7,8,8,9,9,10,10,11,11,12,12-eicosafluorododecyl (meth)acrylate.

The amount of the above fluorine-containing monomer is usually not more than 40% by weight, preferably not more than 30% by weight, more preferably not more than 20% by weight, based on the total amount of copolymerizable components. If such an amount exceeds 40% by weight, the amount of the polysiloxane macromonomer tends to be relatively small, whereby high oxygen permeability and high mechanical strength tend to be hardly expected.

Further, in order to impart improved mechanical strength and durability to the resulting ocular lens material, an additional copolymerizable component to be incorporated, may, for example, be a crosslinking agent such as ethylene glycol di(meth)acrylate, diethylene glycol di(meth)acrylate, triethylene glycol di(meth)acrylate, propylene glycol di(meth)acrylate, dipropylene glycol di(meth)acrylate, allyl (meth)acrylate, vinyl (meth)acrylate, trimethyrolpropane tri(meth)acrylate, methacryloyloxy ethyl acrylate, divinylbenzene, diallyl phthalate, diallyl adipate, triallyl isocyanurate, α-methylene-N-vinylpyrrolidone, 4-vinylbenzyl (meth)acrylate, 3-vinylbenzyl (meth)acrylate, 2,2-bis(p-(meth)acryloyloxyphenyl)hexafluoropropane, 2,2-bis(m-(meth)acryloyloxyphenyl)hexafluoropropane, 2,2-bis(o-(meth)acryloyloxyphenyl)hexafluoropropane, 2,2-bis(p-(meth)acryloyloxyphenyl)propane, 2,2-bis(m-(meth)acryloyloxyphenyl)propane, 2,2-bis(o(meth)acryloyloxyphenyl)propane, 1,4-bis(2-(meth)acryloyloxyhexafluoroisopropyl)benzene, 1,3-bis(2-(meth)acryloyloxyhexafluoroisopropyl)benzene, 1,2-bis(2-(meth)acryloyloxyhexafluoroisopropyl)benzene, 1,4-bis(2-(meth)acryloyloxyisopropyl)benzene, 1,3-bis(2-(meth)acryloyloxyisopropyl)benzene or 1,2-bis(2-(meth)acryloyloxyisopropyl)benzene. These crosslinking agents may be used alone or in combination as a mixture of two or more. The amount of such a crosslinking agent is usually from 0.01 to 10 parts by weight, preferably from 0.05 to 8 parts by weight, more preferably from 0.1 to 5 parts by weight, per 100 parts by weight of the total amount of copolymerizable components. If the amount of the crosslinking agent is less than 0.01 part by weight, no adequate effects tend to be obtained by the incorporation of such such a crosslinking agent. On the other hand, if it exceeds 10 parts by weight, the material tends to be brittle.

Further, in order to impart ultraviolet absorptivity or a color to the resulting ocular lens material, a polymerizable ultraviolet absorber, a polymerizable dyestuff or a polymerizable ultraviolet absorbing dyestuff may, for example, be used as an additional copolymerizable component.

Specific examples of the polymerizable ultraviolet absorber include, for example, benzophenone type polymerizable ultraviolet absorbers such as 2-hydroxy-4-(meth)acryloyloxybenzophenone, 2-hydroxy-4-(meth)acryloyloxy-5-tert-butylbenzophenone, 2-hydroxy-4-(meth)acryloyloxy-2',4'-dichlorobenzophenone and 2-hydroxy-4-(2'-hydroxy-3'-(meth)acryloyloxypropoxy)-benzophenone; benzotriazole type polymerizable ultraviolet absorbers such as 2-(2'-hydroxy-5'-(meth)acryloyloxyethylphenyl)-2H-benzotriazole, 2-(2'-hydroxy-5'-(meth)acryloyloxyethylphenyl)-5-chloro-2H-benzotriazole, 2-(2'-hydroxy-5'-(meth)acryloyloxypropylphenyl)-2H-benzotriazole and 2-(2'-hydroxy-5'-(meth)acryloyloxypropyl-3'-tert-butylphenyl)-5-chloro-2H-benzotriazole; salicylic acid derivative-type polymerizable ultraviolet absorbers such as phenyl 2-hydorxy-4-(meth)acryloyloxymethylbenzoate; and other polymerizable ultraviolet absorbers such as methyl 2-cyano-3-phenyl-3-(3'-(meth)acryloyloxyphenyl)propenoate. These polymerizable ultraviolet absorbers may be used alone or in combination as a mixture of two or more of them.

Specific examples of the polymerizable dyestuff include, for example, azo type polymerizable dyestuffs such as 1-phenylazo-4-(meth)acryloyloxynaphthalene, 1-phenylazo-2-hydroxy-3-(meth)acryloyloxynaphthalene, 1-naphthylazo-2-hydroxy-3-(meth)acryloyloxynaphthalene, 1-(α-anthrylazo)-2-hydroxy-3-(meth)acryloyloxynaphthalene, 1-((4'-(phenylazo)phenyl)azo)-2-hydroxy-3-(meth)acryloyloxynaphthalene, 1-(2',4'-xylylazo)-2-(meth)acryloyloxynaphthalene, 1-(o-tolylazo)-2(meth)acryloyloxynaphthalene, 2-(m-(meth)acryloylamideanilino)-4,6-bis(1'-(o-tolylazo)-2'-naphthylamino)-1,3,5-triazine, 2-(m-vinylanilino)-4-((4'-nitrophenylazo)anilino)-6-chloro-1,3,5-triazine, 2-(1'-(o-tolylazo)-2'-naphthyloxy-4-(m-vinylanilino)-6-chloro-1,3,5-triazine, 2-(p-vinylanilino)-4-(1'-(o-tolylazo)-2'-naphthylamino)-6-chloro-1,3,5-triazine, N-(1'-(o-tolylazo)-2'-naphthyl)-3-vinylphthalic acid monoamide, N-(1'-(o-tolylazo)-2'-naphthyl)-6-vinylphthalic acid monoamide, 3-vinylphthalic acid-(4'-(p-sulfophenylazo)-1'-naphthyl)monoester, 6-vinylphthalic acid-(4'-(p-sulfophenylazo)-1'-naphthyl)monoester, 3-(meth)acryloylamide-4-phenylazophenol, 3-(meth)acryloylamide-4-(8'-hydroxy-3',6'-disulfo-1'-naphthylazo)phenol, 3-(meth)acryloylamide-4-(1'-phenylazo-2'-naphthylazo)phenol, 3-(meth)acryloylamide-4-(p-tolylazo)phenol, 2-amino-4-(m-(2'-hydroxy-1'-naphthylazo)anilino)-6-isopropenyl-1,3,5-triazine, 2-amino-4-(N-methyl-p-(2'-hydroxy-1'-naphthylazo)anilino)-6-isopropenyl-1,3,5-triazine, 2-amino-4-(m-(4'-hydroxy-1'-phenylazo)anilino)-6-isopropenyl-1,3,5-triazine, 2-amino-4-(N-methyl-p-(4'-hydroxyphenylazo)anilino)-6-isopropenyl-1,3,5-triazine, 2-amino-4-(m-(3'-methyl-1'-phenyl-5'-hydroxy-4'-pyrazolylazo)anilino)-6-isopropenyl-1,3,5-triazine, 2-amino-4-(N-methyl-p-(3'-methyl-1'-phenyl-5'-hydroxy-4'-pyrazolylazo)anilino)-6-phenyl-5'-hydroxy-4'-pyrazolylazo)anilino)-6-isopropenyl-1,3,5-triazine, 2-amino-4-(p-phenylazoanilino)-6-isopropenyl-1,3,5-triazine and 4-phenylazo-7-(meth)acryloylamide-1-naphthol; anthraquinone type polymerizable dyestuffs such as 1,5-bis((meth)acryloylamino)-9,10-anthraquinone, 1-(4'-vinylbenzoylamide)-9,10-anthraquinone, 4-amino-1-(4'-vinylbenzoylamide)-9,10-anthraquinone, 5-amino-1-(4'-vinylbenzoylamide)-9,10-anthraquinone, 8-amino-1-(4'-vinylbenzoylamide)-9,10-anthraquinone, 4-nitro-1-(4'-vinylbenzoylamide)-9,10-anthraquinone, 4-hydroxy-1-(4'-vinylbenzoylamide)-9,10-anthraquinone, 1-(3'-vinylbenzoylamide)-9,10-anthraquinone, 1-(2'-vinylbenzoylamide)-9,10-anthraquinone, 1-(4'-isopropenylbenzoylamide)-9,10-anthraquinone, 1-(3'-isopropenylbenzoylamide)-9,10-anthraquinone, 1-(2'-isopropenylbenzoylamide)-9,10-anthraquinone, 1,4-bis-(4'-vinylbenzoylamide)-9,10-anthraquinone, 1,4-bis-(4'-isopropenylbenzoylamide)-9,10-anthraquinone, 1,5-bis-(4'-vinylbenzoylamide)-9,10-anthraquinone, 1,5-bis-(4'-isopropenylbenzoylamide)-9,10-anthraquinone, 1-methylamino-4-(3'-vinylbenzoylamide)-9,10-anthraquinone, 1-methylamino-4-(4'-vinylbenzoyloxyethylamino)-9,10-anthraquinone, 1-amino-4-(3'-vinylphenylamino)-9,10-anthraquinone-2-sulfonic acid, 1-amino-4-(4'-vinylphenylamino)-9,10-anthraquinone-2-sulfonic acid, 1-amino-4-(2'-vinylbenzylamino)-9,10-anthraquinone-2sulfonic acid, 1-amino-4-(3'-(meth)acryloylaminophenylamino)-9,10-anthraquinone-2-sulfonic acid, 1-amino-4-(3'-(meth)acryloylaminobenzylamino)-9,10-anthraquinone-2-sulfonic acid, 1-(β-ethoxycarbonylallylamino)-9,10-anthraquinone, 1-(β-carboxyallylamino)-9,10-anthraquinone, 1,5-di-(β-carboxyallylamino)-9,10-anthraquinone, 1-(β-isopropoxycarbonylallylamino)-5-benzoylamide-9,10-anthraquinone, 2-(3'-(meth)acryloylamide-anilino)-4-(3'-(3''-sulfo-4''-aminoanthraquinon-1''-yl)amino -anilino)-6-chloro-1,3,5triazine, 2-(3'-(meth)acryloylamide-anilino)-4-(3'-(3''-sulfo-4''-aminoanthraquinon -1''-yl)amino-anilino)-6-hydrazino-1,3,5-triazine, 2,4-bis-((4''-methoxyanthraquinon-1''-yl)amino)-6-(3'-vinylanilino)-1,3,5-triazine and 2-(2-'-vinylphenoxy)-4-

(4'-(3''-sulfo-4''-aminoanthraquinon-1''-yl-amino)anilino) -6-chloro-1,3,5-triazine; nitro type polymerizable dyestuffs such as o-nitroanilinomethyl (meth)acrylate; and phthalocyanine type polymerizable dyestuffs such as (meth)acryloyl-modified tetramino copper phthalocyanine and (meth)acryloyl-modified (dodecanoyl-modified tetraamino copper phthalocyanine). These polymerizable dyestuffs may be used alone or in combination as a mixture of two or more of them.

Specific examples of the polymerizable ultraviolet absorbing dyestuff include, for example, benzophenone type polymerizable ultraviolet absorbing dyestuffs such as 2,4-dihydroxy-3-(p-styrenoazo)benzophenone, 2,4-dihydroxy-5-(p-styrenoazo)benzophenone, 2,4-dihydroxy-3-(p-(meth)acryloyloxymethylphenylazo)benzophenone, 2,4-dihydroxy-5-(p-(meth)acryloyloxymethylphenylazo)-benzophenone, 2,4-dihydroxy-3-(p(meth)acryloyloxyethylphenylazo)benzophenone, 2,4-dihydroxy-5-(p-(meth)acryloyloxyethylphenylazo)-benzophenone, 2,4-dihydroxy-3-(p(meth)acryloyloxypropylphenylazo)benzophenone, 2,4-dihydroxy-5-(p-(meth)acryloyloxypropylphenylazo)-benzophenone, 2,4-dihydroxy-3-(o(meth)acryloyloxymethylphenylazo)benzophenone, 2,4-dihydroxy-5-(o-(meth)acryloyloxymethylphenylazo)benzophenone, 2,4-dihydroxy-3-(o(meth)acryloyloxyethylphenylazo)benzophenone, 2,4-dihydroxy-5-(o-(meth)acryloyloxyethylphenylazo)-benzophenone, 2,4-dihydroxy-3-(o-(meth)acryloyloxypropylphenylazo)benzophenone, 2,4-dihydroxy-5-(o-(meth)acryloyloxypropylphenylazo)-benzophenone, 2,4-dihydroxy-3-(p-(N,N-di(meth)acryloyloxyethylamino)phenylazo)benzophenone, 2,4-dihydroxy-5-(p-(N,N-di(meth)acryloyloxyethylamino)-phenylazo)benzophenone, 2,4-dihydroxy-3-(o-(N,N-di(meth)acryloyloxyethylamino)phenylazo)benzophenone, 2,4-dihydroxy-5-(o-(N,N-di(meth)acryloylethylamino)phenylazo)benzophenone, 2,4-dihydroxy-3-(p-(N-ethyl-N-(meth)acryloyloxyethylamino)-phenylazo)benzophenone, 2,4-dihydroxy-5-(p-(N-ethyl-N-(meth)acryloyloxyethylamino)phenylazo)benzophenone, 2,4-dihydroxy-3-(o-(N-ethyl-N-(meth)acryloyloxyethylamino)phenylazo)benzophenone, 2,4-dihydroxy-5-(o-(N-ethyl-N-(meth)acryloyloxyethylamino)phenylazo)benzophenone, 2,4-dihydroxy-3-(p-(N-ethyl-N-(meth)acryloylamino)phenylazo)benzophenone, 2,4-dihydroxy-5-(p-(N-ethyl-N-(meth)acryloylamino)phenylazo)benzophenone, 2,4-dihydroxy-3-(o-(N-ethyl-N-(meth)acryloylamino)-phenylazo)benzophenone and 2,4-dihydroxy-5-(o-(N-ethyl-N-(meth)acryloylamino)phenylazo)benzophenone; and benzoic acid type polymerizable ultraviolet absorbing dyestuffs such as phenyl 2-hydroxy-4-(p-styrenoazo)benzoate. These polymerizable ultraviolet absorbing dyestuffs may be used alone or in combination as a mixture of two or more of them.

The amounts of the above-mentioned polymerizable ultraviolet absorber, polymerizable dyestuff and polymerizable ultraviolet absorbing dyestuff are substantially influenced by the thickness of the lens, and they are preferably not more than 3 parts by weight, more preferably from 0.1 to 2 parts by weight, per 100 parts by weight of the total amount of monomers to be subjected to polymerization. If the amount exceeds 3 parts by weight, the physical properties of the lens such as mechanical strength, tend to deteriorate. Further, in consideration of the toxicity of the ultraviolet absorber or dyestuff, such a material tends to be unsuitable as a material for ocular lenses such as contact lenses which are in direct contact with living tissues or intraocular lenses embedded in living bodies. Further, particularly in the case of a dyestuff, if the amount is too large, the color of the lens tends to be so deep that the transparency decreases, and visible rays tend to be hardly transmitted through the lens.

The polysiloxane macromonomer and the alkyl (meth)acrylamide as well as the siloxane monomer and the additional copolymerizable components are suitably adjusted and subjected to copolymerization depending upon the particularly purpose of the desired ocular lens such as a contact lens or an intraocular lens.

In the present invention, the polysiloxane monomer and the alkyl (meth)acrylamide as well as the siloxane monomer and the additional copolymer components which are used as the case requires, are adjusted to have the desired proportions within the above-mentioned ranges, and a radical polymerization initiator is added thereto, followed by polymerization by a usual method.

The usual method may be a method of gradually heating the mixture after the addition of the radical polymerization initiator at a temperature within a range of from room temperature to about 120° C., or a method of irradiating electromagnetic waves such as microwaves, ultraviolet rays or radiation rays ($\gamma$-rays). In the case of the heat polymerization, the temperature may be stepwisely raised. The polymerization may be conducted by a bulk polymerization method or a solution polymerization method using e.g. a solvent, or it may be conducted by any other method.

Specific examples of the radical polymerization initiator include, for example, azobisisobutylonitrile, azobis-dimethylvaleronitrile, benzoyl peroxide, tert-butyl hydroperoxide and cumene hydroperoxide. These radical polymerization initiators may be used alone or in combination as a mixture of two or more of them. In a case where photopolymerization is employed, a photopolymerization initiator or sensitizer is preferably added. The above-mentioned polymerization initiator or sensitizer is incorporated usually in an amount of from about 0.001 to 2 parts by weight, preferably from 0.01 to 1 part by weight, per 100 parts by weight of the total amount of copolymerizable components.

For the shaping of ocular lenses such as contact lenses or intraocular lenses, shaping methods commonly used by those skilled in the art may be employed. As such shaping methods, there may be mentioned, for example, a lathe cutting and grinding method and a molding method. The cutting and grinding method is a method in which the polymerization is conducted in a suitable mold or vessel to obtain a rod-, block- or plate-shaped base material (polymer), and then the base material is processed into a desired shape by mechanical processing such as cutting, grinding and polishing. The molding method is a method wherein a mold corresponding to the shape of a desired ocular lens is prepared, and the polymerization of the above-mentioned lens components is conducted in this mold to obtain a molded product, which may further be subjected to mechanical finishing treatment, if necessary.

Apart from these methods, it is possible to employ a method for the present invention in which a monomer capable of forming a hard polymer is impregnated in a lens material, and then such a monomer is polymerized to harden the entirety, which is then subjected to cutting and grinding processing, and from a product processed to a desired shape, the hard polymer is removed to obtain a shaped product composed of the lens material (Japanese Unexamined Patent Publications No. 278024/1987 and No. 11854/1989).

Further, when an intraocular lens is to be obtained, a supporting portion of the lens may be prepared separately from the lens and then attached to the lens, or it may be molded simultaneously (integrally) with the lens.

Now, the ocular lens material of the present invention will be described in detail with reference to examples. However, it should be understood that the present invention is by no means restricted to such specific examples.

EXAMPLE 1

20 parts by weight of a urethane bond-containing polysiloxane macromonomer of the formula:

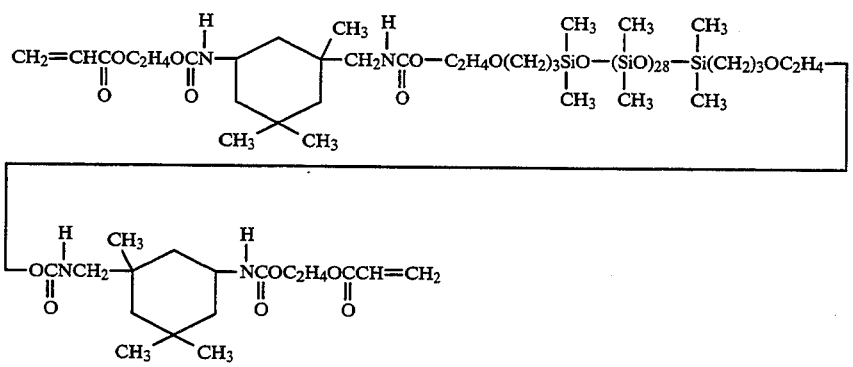

(hereinafter referred to as macromonomer A), 80 parts by weight of N,N-dimethylacrylamide, 0.5 part by weight of ethylene glycol dimethacrylate and 0.1 part by weight of 2,2'-azobis(2,4-dimethylvaleronitrile) as a polymerization initiator, were uniformly mixed to obtain transparent solution. This solution was put into a glass test tube. Then, such a test tube was transferred into a circulation type constant-temperature bath and heated at 35° C. for 40 hours and at 50° C. for 8 hours. Then, it was transferred into an air circulating drier, and polymerization was conducted by raising the temperature to 110° C. at a rate of 10° C. per two hours to obtain a rod-shaped copolymer having a diameter of 13.5 mm.

The obtained rod-shaped copolymer was subjected to hydration treatment and then cut into specimens having a thickness of 0.2 mm, which were then subjected to grinding and polishing treatment to obtain test specimens. Various physical properties of the test specimens were measured in accordance with the following methods. The results are shown in Table 1.

(a) Transparency

A test specimen in water was visually observed and evaluated in accordance with the following evaluation standards.
Evaluation standards
○: Transparent
Δ: Slightly turbid
×: Substantially turbid (b) Flexibility A test specimen was pulled from both sides, and the stretchability was examined and evaluated in accordance with the following evaluation standards.
Evaluation standards
○: Very well stretched
Δ: Not stretched very well
×: Not substantially stretched (c) Tackiness A test specimen was touched with a finger, and the releasability from the test specimen was examined and evaluated in accordance with the following evaluation standards.
Evaluation standards
○: Finger readily released
Δ: Finger slightly hardly released
×: Finger hardly released (d) Penetration strength By means of a penetration strength tester, a pressing needle having a diameter of 1/16 inch was pressed against the center of a test specimen, and the load (g) at the time of the breakage of the test specimen was measured. However, the values listed in Table 1 are values calculated as the thickness of the test specimen was 0.2 mm.

(e) Elongation

The elongation (%) at the time of the breakage of the test specimen in the above-mentioned measurement of the penetration strength (g), was measured.

(f) Oxygen permeability coefficient ($DK_{0.2}$)

The oxygen permeability coefficient of a test specimen was measured in a physiological saline at 35° C. by means of Seikaken Type film oxygen permeability measuring instrument manufactured by Rika Seiki Kogyo Kabushiki Kaisha. The unit for oxygen permeability coefficient is $ml(STP)\text{-}cm^2/(cm^3 \cdot sec \cdot mmHg)$. The oxygen permeability coefficients in Table 1 are numerical values obtained by multiplying the values of the oxygen permeability coefficients with the thickness of the test specimens being 0.2 nun by $10^{11}$.

(g) Water content

A test specimen was subjected to hydration treatment, and then the water content (wt%) of the test specimen was measured in accordance with the following equation:

$$\text{Water content (wt \%)} = \frac{W - W_o}{W} \times 100$$

where W is the weight (g) of the test specimen upon absorption of water to the equilibrium state after the hydration treatment, and Wo is the weight (g) of the above-mentioned test specimen which was dried to the dried state in a drier after the hydration treatment.

(h) Refractive index ing treatment to obtain test specimens. Various physical properties of the obtained test specimens were examined in the same manner as in Example 1. The results are shown in Table 1.

TABLE 1

| Example Nos. | 1 | 2 | 3 | 4 | 5 | 6 | 7 | 8 | 9 | 10 | 11 | 12 | 13 | 14 |
|---|---|---|---|---|---|---|---|---|---|---|---|---|---|---|
| Composition (parts by weight) | | | | | | | | | | | | | | |
| Macromonomer A | 20 | 40 | 50 | 60 | 80 | 54 | 33 | 66 | 13 | 54 | 42 | 33 | 17 | 66 |
| DMAA | 80 | 60 | 50 | 40 | 20 | 13 | 33 | 17 | 54 | 13 | 42 | 33 | 66 | 17 |
| SiMA | — | — | — | — | — | 33 | 34 | 17 | — | — | — | — | — | — |
| SiSt | — | — | — | — | — | — | — | — | 33 | 33 | 16 | 34 | 17 | 17 |
| EDMA | 0.5 | 0.5 | 0.5 | 0.5 | 0.5 | 0.5 | 0.5 | 0.5 | 0.5 | 0.5 | 0.5 | 0.5 | 0.5 | 0.5 |
| V-65 | 0.1 | 0.1 | 0.1 | 0.1 | 0.1 | 0.1 | 0.1 | 0.1 | 0.1 | 0.1 | 0.1 | 0.1 | 0.1 | 0.1 |
| Physical properties | | | | | | | | | | | | | | |
| Transparency | ◯ | ◯ | ◯ | ◯ | ◯ | ◯ | ◯ | ◯ | ◯ | ◯ | ◯ | ◯ | ◯ | ◯ |
| Flexibility | ◯ | ◯ | ◯ | ◯ | ◯ | ◯ | ◯ | ◯ | ◯ | ◯ | ◯ | ◯ | ◯ | ◯ |
| Tackiness | ◯ | ◯ | ◯ | ◯ | ◯ | ◯ | ◯ | ◯ | ◯ | ◯ | ◯ | ◯ | ◯ | ◯ |
| Penetration strength (g) | 136 | 182 | 231 | 99 | 64 | 251 | 224 | 279 | 318 | 923 | 233 | 769 | 195 | 314 |
| Elongation (%) | 49 | 36 | 33 | 10 | 5 | 61 | 68 | 33 | 65 | 42 | 33 | 105 | 59 | 36 |
| Oxygen permeability coefficient (DK 0.2) | 45 | 39 | 83 | 85 | 119 | 77 | 79 | 86 | 35 | 57 | 71 | 79 | 33 | 72 |
| Water content (wt %) | 59 | 50 | 38 | 23 | 14 | 13 | 28 | 19 | 47 | 10 | 40 | 25 | 60 | 15 |
| Refractive index | 1.393 | 1.409 | 1.422 | 1.423 | 1.423 | 1.439 | 1.429 | 1.437 | 1.414 | 1.449 | 1.410 | 1.444 | 1.396 | 1.440 |
| Lipid stain resistance | B | B | B | B | B | B | B | B | B | B | B | B | B | B |

The refractive index was measured at a temperature of 25° C. under a relative humidity of 50% by means of Atago refractometer 1T, manufactured by Kabushiki Kaisha Atago.

(i) Lipid stain resistance (Test on deposition of lauric acid on the surface)

0.2 g of lauric acid ($CH_3(CH_2)_{10}COOH$) and 100 ml of distilled water were put into a 100 ml Erlenmeyer flask and then heated and stirred at about 50° C. to obtain a dispersion of lauric acid. Then, a hydrated test specimen was put into the dispersion and stirred for 10 minutes. The test specimen was taken out and gently rinsed with distilled water of about 50° C., and then it was permitted to dry naturally. Then, the degree of deposition of lauric acid was visually observed and evaluated in accordance with the following evaluation standards.

Evaluation standards
- A: No deposition (stain) of lauric acid is observed on the surface of the test specimen, and there is no difference when compared with poly(2-hydroxyethyl methacrylate) (hereinafter referred to simply as PHEMA) which is particularly excellent in lipid stain resistance among commonly employed soft contact lens materials.
- B: A stain is slightly observed on the surface of the test specimen, but there is no difference as compared with PHEMA.
- C: A stain is observed on the surface of the test specimen, but there is no significant difference as compared with PHEMA.
- D: A stain is distinctly observed on the surface of the test specimen, and there is a significant difference as compared with PHEMA.
- E: A substantial stain is observed on the surface of the test specimen, and there is an apparent significant difference as compared with PHEMA.

EXAMPLES 2 TO 14

In the same manner as in Example 1, various components were blended to have compositions as identified in Table 1 and polymerized to obtain rod-shaped copolymers, which were then subjected to grinding and polishing treatment to obtain test specimens. Various physical properties of the obtained test specimens were examined in the same manner as in Example 1. The results are shown in Table 1.

The abbreviations used in Table 1 and in Table 2 given hereinafter have the following meanings:
DMAA: N,N-dimethylacrylamide
SiMA: Tris(trimethylsiloxy)silylpropyl methacrylate
SiSt: Tris(trimethylsiloxy)silylstyrene
EDMA: Ethylene glycol dimethacrylate
V-65: 2,2'-azobis(2,4-dimethylvaleronitrile)

It is evident from the results shown in Table 1 that the ocular lens materials of Examples 1 to 14 were obtained by using urethane bond-containing silicone macromonomers. Such macromonomers not only have urethane bonds at both terminals but also have urethane bonds optionally introduced at intermediate portions of the silicone chains, whereby such ocular lens materials have high oxygen permeability and high mechanical strength. Further, as they employ an alkyl (meth)acrylamide, they are also excellent in the transparency, the water content and the lipid stain resistance.

Further, the ocular lens materials of Examples 6 to 14 further employ a silicon-containing alkyl (meth)acrylate or a silicon-containing styrene derivative, whereby it is evident that the mechanical strength and the oxygen permeability are further improved.

COMPARATIVE EXAMPLE 1

A rod-shaped copolymer was prepared in the same manner as in Example 1 except that in Example 1, 100 parts by weight of macromonomer A was used without using N,N-dimethylacrylamide. It was attempted to prepared a test specimen by grinding this copolymer, but it was impossible to grind the copolymer, since it was too soft.

COMPARATIVE EXAMPLE 2

A rod-shaped copolymer was prepared in the same manner as in Example 1 except that in Example 1, 100 parts by weight of N,N-dimethylacrylamide was used without using macromonomer A, and it was subjected to grinding and polishing treatment to obtain a test specimen. The penetration strength of this test specimen was measured in the same manner as in Example i and found to be almost 0 g. Thus, the copolymer was found to be useless as an ocular lens material.

COMPARATIVE EXAMPLE 3

A copolymer was prepared in the same manner as in Example 5 except that in Example 5, 80 parts by macromonomer B of the formula:

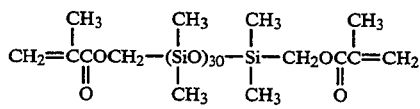

was used instead of macromonomer A. However, such a copolymer was turbid and not suitable as an ocular lens material.

EXAMPLES 15 TO 28

In the same manner as in Example 1, various components were blended to have compositions as identified in Table 2 and polymerized to obtain rod-shaped copolymers, which were then subjected to grinding and polishing treatment to obtain test specimens. Various physical properties of the obtained test specimens were examined in the same manner as in Example 1. The results are shown in Table 2.

In Examples 15 to 28, the more the amount of DMAA incorporated, and in Examples 23 to 28, the more the amount of the macromonomer which is a polysiloxane macromonomer having a fluoroalkyl group, incorporated, the higher the degree of improvement in the lipid stain resistance of the resulting ocular lens material.

TABLE 2

| Example Nos. | 15 | 16 | 17 | 18 | 19 | 20 | 21 | 22 | 23 | 24 | 25 | 26 | 27 | 28 |
|---|---|---|---|---|---|---|---|---|---|---|---|---|---|---|
| Compositions (parts by weight) | | | | | | | | | | | | | | |
| Macromonomer A | 20 | 10 | 20 | 10 | 10 | 20 | 10 | 10 | — | — | — | — | — | — |
| Macromonomer C | — | — | — | — | — | — | — | — | 10 | 20 | 10 | 20 | 10 | 20 |
| DMAA | 30 | 30 | 40 | 40 | 43 | 50 | 45 | 50 | 30 | 30 | 40 | 40 | 50 | 50 |
| SiMA | 50 | 60 | 40 | 50 | 47 | 30 | 45 | 40 | 60 | 50 | 50 | 40 | 40 | 30 |
| EDMA | 0.5 | 0.3 | 0.5 | 0.3 | 0.3 | 0.5 | 0.3 | 0.3 | 0.5 | 0.5 | 0.5 | 0.5 | 0.5 | 0.5 |
| V-65 | 0.1 | 0.1 | 0.1 | 0.1 | 0.1 | 0.1 | 0.1 | 0.1 | 0.1 | 0.1 | 0.1 | 0.1 | 0.1 | 0.1 |
| Physical properties | | | | | | | | | | | | | | |
| Transparency | ○ | ○ | ○ | ○ | ○ | ○ | ○ | ○ | ○ | ○ | ○ | ○ | ○ | ○ |
| Flexibility | ○ | ○ | ○ | ○ | ○ | ○ | ○ | ○ | ○ | ○ | ○ | ○ | ○ | ○ |
| Tackiness | ○ | ○ | ○ | ○ | ○ | ○ | ○ | ○ | ○ | ○ | ○ | ○ | ○ | ○ |
| Penetration strength (g) | 386 | 382 | 185 | 393 | 173 | 174 | 159 | 196 | 324 | 234 | 199 | 161 | 128 | 153 |
| Elongation (%) | 121 | 131 | 62 | 169 | 120 | 51 | 91 | 86 | 117 | 73 | 94 | 54 | 61 | 44 |
| Oxygen permeability coefficient (DK 0.2) | 98 | 98 | 70 | 80 | 77 | 46 | 73 | 56 | 68 | 79 | 62 | 65 | 62 | 50 |
| Water content (wt %) | 19 | 17 | 32 | 33 | 35 | 44 | 38 | 44 | 16 | 20 | 32 | 31 | 44 | 43 |
| Refractive index | 1.438 | 1.440 | 1.427 | 1.428 | 1.427 | 1.415 | 1.427 | 1.414 | 1.440 | 1.436 | 1.427 | 1.426 | 1.416 | 1.415 |
| Lipid stain resistance | B | B | B | B | B | B | B | B | A | A | A | A | A | A |

COMPARATIVE EXAMPLE 4

A copolymer was prepared in the same manner as in Example 3 except that in Example 3, 50 parts by weight of macromonomer B was used instead of macromonomer A. However, such a copolymer was turbid and not suitable as an ocular lens material.

COMPARATIVE EXAMPLE 5

A copolymer was prepared in the same manner as in Example 1 except that in Example 1, 20 parts of macromonomer B was used instead of macromonomer A. However, such a copolymer was turbid and not suitable as an ocular lens material.

In Table 2, macromonomer C is the compound of the formula:

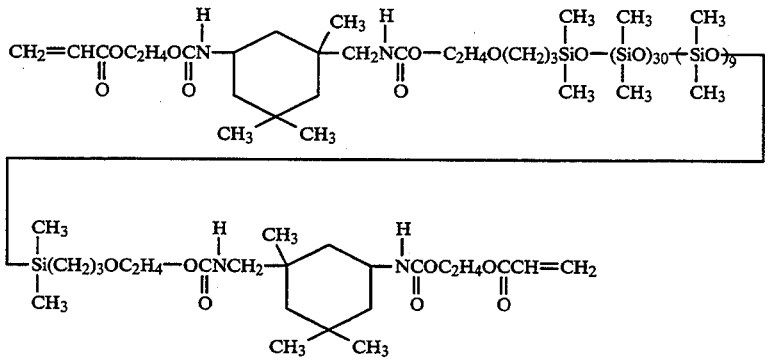

It is evident from the results shown in Table 2 that the ocular lens materials obtained in Examples 15 to 28 have high oxygen permeability and excellent mechanical strength and exhibit water-absorptivity, and they are also excellent in the transparency and lipid stain resistance.

The ocular lens materials obtained in Examples 23 to 28 are those prepared by using a polysiloxane macromonomer having a fluoroalkyl group, whereby it is evident that the lipid stain resistance is further improved over those obtained by using a polysiloxane macromonomer having no fluoroalkyl group, due to the action of reducing the critical surface tension, which a fluorine atom usually has.

The ocular lens material of the present invention provides the following effects.

(a) The ocular lens material of the present invention is excellent in the transparency, and it provides an effect that it is suitable for use as an ocular lens.

(b) The ocular lens material of the present invention is excellent in the oxygen permeability, and it provides an effect that when it is formed into a contact lens, it is free from impairing the metabolic function of cornea.

(c) The ocular lens material of the present invention has practically adequate mechanical strength and relatively good rubber elasticity, and it provides an effect that it can be formed into a lens which is excellent in the dimensional stability and which is free from breakage against various physical treatments.

(d) The ocular lens material of the present invention shows substantial water absorptivity (water content of at least 5% by weight), and it is soft in a hydrated state. Thus, it provides an effect that when formed into a contact lens, it gives comfortable feeling to the wearer, and when formed into an intraocular lens, it can be folded and inserted through a small incision of the eye ball without damaging the ocular tissues.

(e) The ocular lens material of the present invention has little surface tackiness, and it is excellent in lipid stain resistance.

(f) The ocular lens material of the present invention is relatively hard in a non-water containing state, and it has an effect that in such a state, cutting and grinding treatment can readily be applied thereto, and fine precision treatment can be applied thereto.

We claim:

1. An ocular lens material made of a copolymer comprising, as main copolymerizable components (A) a polysiloxane macromonomer having polymerizable groups bonded via one or more urethane bonds to the siloxane main chain, of the formula (I):

$$A^1-U^1-S^1-U^2-A^2- \quad (I)$$

wherein $A^1$ is a group of the formula (II):

$$Y^{21}-R^{31}- \quad (II)$$

wherein $Y^{21}$ is an acryloyloxy group, a methacryloyloxy group, a vinyl group or an allyl group, and $R^{31}$ is a linear or branched alkylene group having from 2 to 6 carbon atoms;

$A^2$ is a group of the formula (III):

$$-R^{34}-Y^{22} \quad (III)$$

wherein $Y^{22}$ is an acryloyloxy group, a methacryloyloxy group, a vinyl group or an allyl group, and $R^{34}$ is a linear or branched alkylene group having from 2 to 6 carbon atoms;

$U^1$ is a group of the formula (IV):

$$-X^{21}-E^{21}-X^{25}-R^{32}- \quad (IV)$$

wherein $X^{21}$ is a covalent bond, an oxygen atom or an alkylene glycol group having from 1 to 6 carbon atoms, $E^{21}$ is —CONH— (provided that in this case, $X^{21}$ is a covalent bond, and $E^{21}$ forms an urethane bond together with $X^{25}$) or a bivalent group derived from a diisocyanate selected from the group consisting of saturated or unsaturated aliphatic, alicyclic and aromatic diisocyanates (provided in that this case, $X^{21}$ is an oxygen atom or an alkylene glycol group having from 1 to 6 carbon atoms, and $E^{21}$ forms an urethane bond together with $X^{21}$ and $X^{25}$), $X^{25}$ is an oxygen atom or an alkylene glycol group having from 1 to 6 carbon atoms, and $R^{32}$ is a linear or branched alkylene group having from 1 to 6 carbon atoms;

$S^1$ is a group of the formula (V):

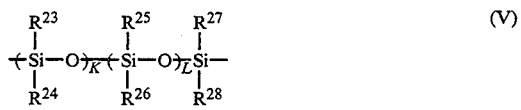

wherein each of $R^{23}$, $R^{24}$, $R^{25}$, $R^{26}$, $R^{27}$ and $R^{28}$ independently represents an alkyl group having from 1 to 6 carbon atoms, a fluoroalkyl group or a phenyl group, K is an integer of from 1 to 50, and L is an integer of from 0 to (50−K);

$U^2$ is a group of the formula (VI):

$$-R^{33}-X^{26}-E^{22}-X^{22}- \quad (VI)$$

wherein $R^{33}$ is a linear or branched alkylene group having from 1 to 6 carbon atoms, $X^{22}$ is a covalent bond, an oxygen atom or an alkylene glycol group having from 1 to 6 carbon atoms, $X^{26}$ is an oxygen atom or an alkylene glycol group having from 1 to 6 carbon atoms, and $E^{22}$ is —CONH (provided that in this case, $X^{22}$ is a covalent bond, and $E^{22}$ forms an urethane bond together with $X^{26}$) or a bivalent group derived from a diisocyanate selected from the group consisting of aturated or unsaturated aliphatic, alicyclic and aromatic diisocyanate (provided that in this case, $X^{22}$ is an oxygen atom or an alkylene glycol group having from 1 to 6 carbon atoms, and $E^{22}$ forms an urethane bond together with $X^{22}$; and $X^{26}$); and (B) an alkyl (meth)acrylamide, wherein the weight ratio of the polysiloxane macromonomer to the alkyl (meth)acrylamide is from 5/95 to 90/10, having a water content of at least 5% and the total amount of the polysiloxane macromonomer and the alkyl (meth)acrylamide is at least 25% by weight.

2. The ocular lens material according to claim 1, wherein the alkyl (meth)acrylamide is N,N-dimethyl methacrylamide.

3. The ocular lens material according to claim 1 or 2, wherein the copolymer contains, as a further copolymerizable component, a silicon-containing monomer selected from the group consisting of a silicon-containing alkyl (meth)acrylate and a silicon-containing styrene derivative, in an amount of not more than 75% by weight, based on the total amount of copolymerizable components.

4. The ocular lens material according to claim 3, wherein the silicon-containing monomer is a silicon-containing styrene derivative.

5. The ocular lens material according to claim 3 or 4, wherein the silicon-containing styrene derivative is tris(trimethylsiloxy)silylstyrene.

6. The ocular lens material according to claim 3, wherein the silicon-containing monomer is a silicon-containing alkyl (meth)acrylate.

7. The ocular lens material according to claim 3 or 6, wherein the silicon-containing alkyl (meth)acrylate tris(trimethylsiloxy)silylpropyl (meth)acrylate.

* * * * *